United States Patent [19]

Okubo

[11] 4,446,733
[45] May 8, 1984

[54] STRESS CONTROL IN SOLID MATERIALS
[75] Inventor: Shigeo Okubo, Menlo Park, Calif.
[73] Assignee: Design Professionals Financial Corporation, Monterey, Calif.
[21] Appl. No.: 293,751
[22] Filed: Aug. 17, 1981
[51] Int. Cl.³ .......................................... G01H 13/00
[52] U.S. Cl. ..................................................... 73/579
[58] Field of Search .............. 73/579, 577, 578, 587; 148/12.9

[56] References Cited

U.S. PATENT DOCUMENTS

| | | | |
|---|---|---|---|
| 2,675,698 | 4/1954 | Johnson | 73/579 |
| 3,600,934 | 8/1971 | Hendrix et al. | 73/577 |
| 3,741,820 | 6/1973 | Hebel, Jr. et al. | 148/12.9 |
| 4,128,011 | 12/1978 | Savage | 73/579 |
| 4,309,903 | 1/1982 | Ono | 73/587 |
| 4,314,202 | 2/1982 | Okubo | 73/658 |
| 4,381,673 | 5/1983 | Klauba et al. | 73/579 |
| 4,383,446 | 5/1983 | Roeder et al. | 73/579 |

Primary Examiner—Stephen A. Kreitman
Attorney, Agent, or Firm—Townsend and Townsend

[57] ABSTRACT

A method of and apparatus for inducing stresses in solid materials in such a manner as to find application to stress relieving and fatigue testing procedures, and a procedure of non-destructively testing structural elements after they are in place within a larger structure. The present invention utilizes the higher resonant modes of vibration of the workpiece or structure undergoing treatment or testing to induce stress waves having maximum moment at many locations distributed over the surface.

13 Claims, 3 Drawing Figures $l$ = 30 UNITS
A = 25 UNITS
$\rho = \dfrac{1}{\pi^2} \dfrac{l^2}{A}$ = 3.65 UNITS
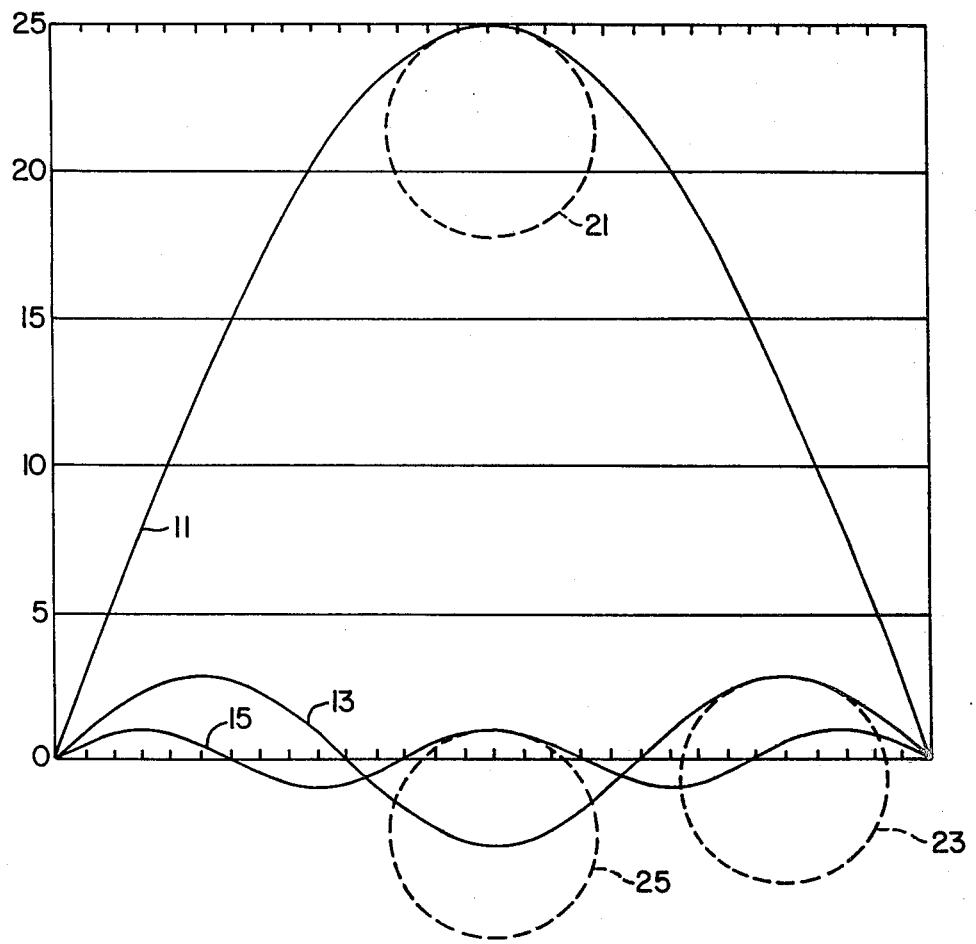
FIG._1.

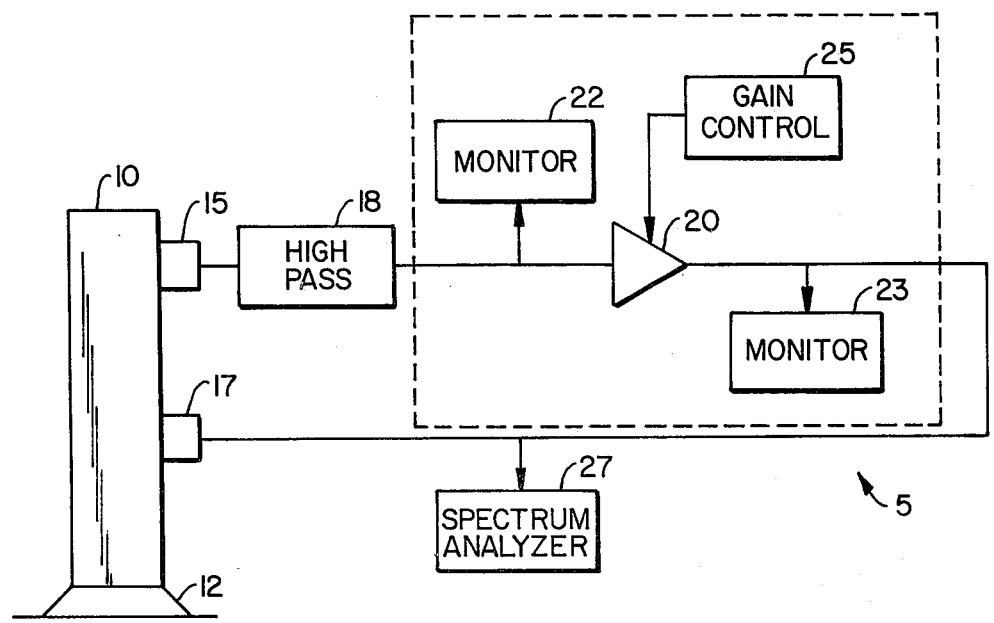
FIG._2.
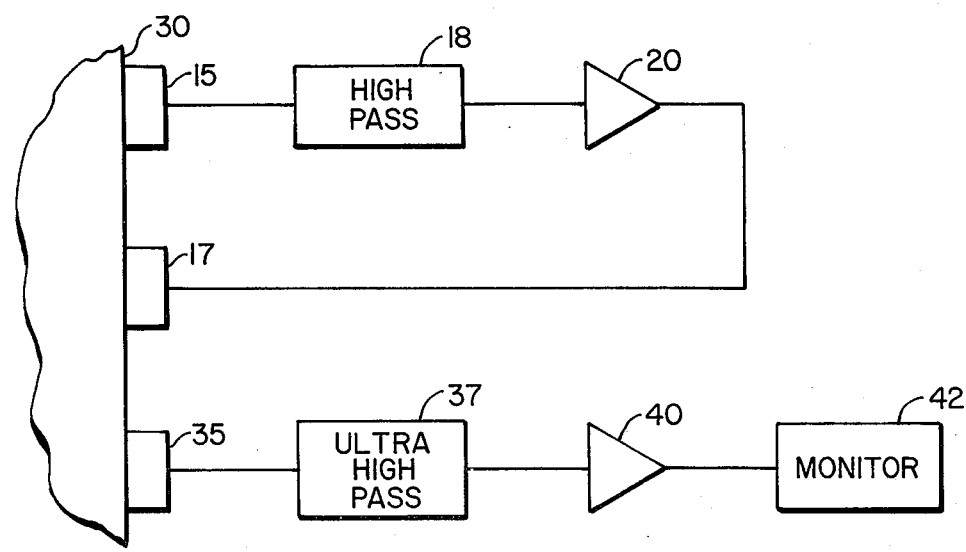
FIG._3.

STRESS CONTROL IN SOLID MATERIALS

FIELD OF THE INVENTION

The present invention relates generally to the stress characteristics of structural materials, and more specifically to a method and apparatus for high frequency stressing of materials for testing and treating purposes.

BACKGROUND OF THE INVENTION

The behavior of structures and structural materials under various stress conditions is of utmost importance for safety and efficiency considerations, and such considerations are at the heart of any structural design. It is known to subject structural elements to stress under controlled conditions for the purpose of controlling the stress distribution within the structure or for testing the structure's behavior under stresses. The former group of activities includes such areas as stress relieving while the latter encompasses fatigue testing and the like.

Consider, for example, stress relieving. As is well known, structural elements are subjected to various fabrication steps that tend to set up non-homogeneous stress conditions within the material. For example, cutting tools used during machining procedures introduce large residual stresses in the workpiece; localized heating during welding induces residual stresses, typically at the exposed toe of the welds; bending loads produce work hardening effects, typically near the surface of the materials.

Vibratory stress relieving devices are known. Such devices comprise a large test stand which is excited by means of a motor-driven unbalanced mass to subject the workpiece to a controlled reversing stress cycle. More particularly, the vibration induces stresses in excess of the residual stresses to be relieved. The vibration causes periodic reversal of these stresses, and the magnitude of the vibration is lowered in order to relieve the initial stresses, in a manner analogous to the well-known demagnetizing procedure. As can be readily appreciated, most vibratory stress relieving machinery is large and requires a considerable amount of power for operation.

Most fatigue testing procedures make use of large machines to subject the structural element under test to relatively low frequency oscillating loads at various stress levels. Fatigue life is then defined in terms of the total number of cycles undergone before failure occurs. The procedure is time-consuming in view of the fact that the structural element typically must be subjected to a large number of cycles before failure occurs. For example, subjecting a beam to a complete bending cycle at a rate of once per second would require approximately 28 hours to generate 100,000 cycles. Many tests require in excess of 1,000,000 cycles.

Aside from the cumbersome special machinery required, the above procedures suffer from an inability to reliably generate the controlled stresses at the locations where the controlled stresses would be most effective. For example, in stress relieving, the stresses induced by the vibrations are not necessarily maximized at the random locations of maximum residual stress within the structural element. Similarly, the fatigue testing procedures do not always apply the greatest stresses at the points of inhomogeneity and discontinuity in the crystal lattice which are most likely to fail under actual dynamic loads.

Once a structural element has been incorporated into a larger structure such as a bridge or building, it can, as a general matter, only be hoped that the element was appropriately stress relieved and that its fatigue characteristics were known to be appropriate. There are methods of non-destructively testing structural elements once in place, such as visual, magnetic, ultrasonic, and X-ray inspection. However, such methods tend to discover defects only after they have long passed the potential stage and have elevated themselves to present dangers. While it is also known to non-destructively test elements by stressing them and sensing high frequency acoustic emissions, it is typically very difficult to apply sufficiently high loads to such elements once they are in place within a larger structure.

In spite of the above problems, mercifully few buildings and bridges collapse, although the consequences of such collapse are inevitably catastrophic. Presumably, buildings and bridges are being sufficiently overdesigned that the lack of precise stress control in the fabricating and testing of the structural elements does not represent a safety problem. It does represent an economic waste, however.

SUMMARY OF THE INVENTION

The present invention provides a method of and apparatus for inducing stresses in solid materials, in such a manner as to find application to stress relieving and fatigue testing procedures. Moreover, the present invention provides a method of non-destructively load testing structural elements after they are in place within a larger structure.

In its broadest aspect, the present invention utilizes the higher resonant modes of vibration of the workpiece or structure undergoing treatment or testing to induce stress waves having maximum moment at many locations evenly distributed over the surface. In accordance with the present invention, a structural element or workpiece is subjected to an excitation, such as an impulse, in order to induce vibrations at the various resonant frequencies characteristic of the structure, i.e., to excite the various resonant modes. The resonant vibrations are sensed by a detecting transducer and a signal having components at a large number of the resonant frequencies is generated. At least one of the high frequency resonant components is amplified to produce an excitation signal which is then applied to appropriate driving transducers that induce stress waves in the structure. Depending on the transducer geometry, bending as well as torsional shear modes may be induced. At each of the higher modes, the distributed locations on the structure surface are subjected to their maximum stress at the same time.

A dynamic stress relieving procedure according to the present invention utilizes a transducer located to introduce a controlled reversing stress cycle and thus effect a relaxation of the stresses in close proximity to the area of residual stresses. A sensor responsive to the radius of curvature of the stressed element being treated is utilized to measure the response of the structural element, and the sensor output forms the basis for the excitation signal, while the depth of the stress penetration is varied by choosing different ranges of the high frequency modes.

An accelerated fatigue testing procedure according to the present invention utilizes small amplitude oscillations of the high resonant frequencies to produce the same maximum cyclic stress level as would be produced by a large amplitude, low frequency bending cycle.

While the high frequency stress excitations are confined generally near the surface of the material, that is where most fatigue failures occur since that is where the maximum stresses due to bending occur. Therefore, the present invention avoids the necessity of exciting the structural element throughout its entire volume to bring about fatigue. Rather, the use of high frequency stress excitations allows large areas of the structural element to be subjected to the stresses with a relatively small energy input. Since the differences in frequencies between the modes approach a constant value at the high frequencies, independently of the manner in which the structural element is supported, the use of high frequency excitations eliminates any critical dependence on the manner in which the structural element is supported in a fixture, and provides highly reproducible results.

A non-destructive procedure for testing structural elements once in place according to the present invention utilizes the high frequency vibrational modes to subject the entire surface of the structural element to stresses. The structural element is scanned for high frequency acoustic emissions to detect surface microfractures that eventually could grow into cracks.

The use of the high frequency resonant modes provides a number of surprising advantages that render the present invention more efficient and effective than the prior art described above. These advantages may be seen more clearly with reference to the theoretical discussion set forth at a later portion of this specification, but will be summarized immediately below.

The higher modes of vibration are characterized by a large number of points of maximum moment evenly distributed over the surface. Since the maximum moments are the same for all modes, and thus the maximum stresses are the same for all modes, substantially the entire surface of the structural element may be subjected to stress waves. Therefore, whether the procedure is a stress relieving or fatigue testing procedure, more reliable coverages are obtained. Since the higher mode frequencies are generally evenly spaced relatively independently of boundary conditions, the present invention is useful in a wide variety of geometrical configurations.

Since the actual amplitude of vibration decreases for the higher modes, the energy input required to excite a given higher mode for the same maximum moment is reduced. Therefore, the present invention avoids the need for the large machines required by the prior art to achieve the high stresses necessary for stress relief or fatigue testing. Similarly, the present invention makes it possible to subject the structural element once in place to the stress levels needed to cause acoustic emissions.

An additional advantage, especially applicable to fatigue testing, is that the high frequencies are characterized by a correpondingly short period for a complete cycle. Therefore, a workpiece may be subjected to a large number of stress cycles within a short time. For example, the same 100,000 cycles that require 28 hours at one bending cycle per second may be achieved in one second when the excitations are in the frequency range of hundreds of kilohertz. The use of the higher resonant modes for fatigue testing has the additional advantage that it simulates very well the dynamic loads under which the element is most likely to fail, since it is typically resonant vibrations rather than dead loads that cause failure.

For a further understanding of the nature and advantages of the present invention, reference should be made to the remaining portions of the specification and to the attached drawings.

BRIEF DESCRIPTION OF THE DRAWINGS

FIG. 1 is a graphical plot of the first three harmonics in a typical case, illustrating the equality of the maximum curvature for the harmonics;

FIG. 2 is a schematic illustration of the present invention as used for carrying out dynamic stress relieving and accelerated fatigue testing procedures; and FIG. 3 is a schematic illustration of the present invention as used for nondestructively testing structural elements in place.

DETAILED THEORETICAL DISCUSSION

As discussed above, the present invention contemplates inducing stress waves in the structural element being treated, and utilizing the higher modes of vibration. Stress is not transmitted instantaneously throughout the structure, but rather, the stress waves travel with characteristic velocities, causing a time varying response. The response is usually detected and described in terms of displacement (y), velocity (dy/dt), acceleration ($d^2y/dt^2$), and jerk ($d^3y/dt^2$). As an example, the equation of motion for the lateral displacement y(x, t) of a beam having length L is given by:

$$\frac{d^2y}{dt^2} + a^2\frac{d^4y}{dx^4} = 0 \qquad (1)$$

where
$a^2 \equiv \epsilon Ig/A\gamma$
$\epsilon I$ = flexural rigidity
A = area of cross section
$\gamma$ = density of material
g = acceleration of gravity.

Assume that the time dependence of the displacement is harmonic, being given by:

$$y = X(x)(A\cos(\omega t) + B\sin(\omega t))$$

$$\frac{d^4X}{dx^4} = k^4X \qquad (2)$$

where $$k^4 = \frac{\omega^2}{a^2} = \frac{\omega^2 A\gamma}{\epsilon Ig}$$

Further assume that the position dependent deflection curve, X, may be expressed by:

$$X = c_1\sin(kx) + c_2\cos(kx) + c_3\sinh(kx) + c_4\cosh(kx) \qquad (3)$$

For a simply supported beam (ends hinged), both deflection and moment (curvature) are zero at x=0 and x=L.

$$(X)_{x=0} = 0 \qquad \left(\frac{d^2X}{dx^2}\right)_{x=0} = 0$$

$$(X)_{x=L} = 0 \quad \left(\frac{d^2X}{dx^2}\right)_{x=L} = 0$$

Using these boundary conditions, the constants are evaluated.

$$c_2 = c_3 = c_4 = 0.$$

This leads to the condition:

$$\sin(kL) = 0.$$

The consecutive roots of $\sin(kl) = 0$ are: $kL = \pi, 2\pi, 3\pi$, etc., so that suitable values of $\omega$ and $k$ are $$\omega_1 = a\frac{\pi^2}{L^2}, \quad \omega_2 = a\frac{4\pi^2}{L^2}, \quad \omega_3\, a\frac{9\pi^2}{L^2}, \text{ etc.} \tag{4}$$

$$k_1 = \frac{\pi}{L}, \quad k_2 = \frac{2\pi}{L}, \quad k_3 = \frac{3\pi}{L}, \text{ etc.}$$

Using the values of k, X may be seen to be a superposition of sinusoidal components $$X_1 = D_1 \sin\left(\frac{\pi x}{L}\right), \quad X_2 = D_2 \sin\left(\frac{2\pi x}{L}\right),$$

$$X_3 = D_3 \sin\left(\frac{3\pi x}{L}\right), \text{ etc.}$$

Thus, the following general functional form for y is obtained:

$$y = \sum_{n=1}^{\infty} \sin\left(\frac{n\pi x}{L}\right)(C_n \cos(\omega_n t) + D_n \sin(\omega_n t)) \tag{5}$$

The particular superposition of such sinusoidal components depends on the initial conditions. For an initial condition of $$(y)_{t=0} = f(x), \quad \left(\frac{dy}{dt}\right)_{t=0} = f_1(x),$$

the solution is given by the well-known Fourier expansion as follows:

$$(y)_{t=0} = f(x) = \sum_{n=1}^{\infty} C_n \sin\left(\frac{n\pi x}{L}\right)$$

$$\left(\frac{dy}{dt}\right)_{t=0} = f_1(x) = \sum_{n=1}^{\infty} D_n \omega_n \sin\left(\frac{n\pi x}{L}\right)$$

$$C_n = \frac{2}{L} \int_0^L f(x) \sin\left(\frac{n\pi x}{L}\right) dx$$

$$D_n = \frac{2}{\omega_n L} \int_0^L f_1(x) \sin\left(\frac{n\pi x}{L}\right) dx$$

For an impact with initial velocity v to a short portion of length $\delta$ of the bar at a distance c from the left support:

$$C_n = 0 \quad D_n = \frac{2}{\omega_n L} v \delta \sin\left(\frac{n\pi c}{L}\right) \tag{6}$$

or, $$y = \frac{2v\delta}{L} \sum_{n=1}^{\infty} \frac{1}{\omega_n} \sin\left(\frac{n\pi c}{L}\right) \sin\left(\frac{n\pi x}{L}\right) \sin(\omega_n t)$$

For $c = L/2$, only the odd harmonics are generated, and y may be expressed as follows:

$$y = \frac{2v\delta}{L} \sum_{i=0}^{\infty} \frac{(-1)^i}{(\omega_{(2i+1)})^2} \sin\left(\frac{(2i+1)x}{L}\right) \sin(\omega_{(2i+1)}t) \tag{7}$$

$$= \frac{2v\delta L}{a\pi^2} \sum_{i=0}^{\infty} \frac{(-1)^i}{(2i+1)^2} \sin\left(\frac{(2i+1)x}{L}\right) \sin(\omega_{(2i+1)}t)$$

$$= A \sum_{i=0}^{\infty} \frac{(-1)^i}{(2i+1)^2} \sin\left(\frac{(2i+1)x}{L}\right) \sin(\omega_{(2i+1)}t)$$

where $A = 2v\delta L/a\pi^2$

While the preceding is well known, certain features and properties, now to be described, are not. Differentiating Equation 7 twice with respect to x leads to:

$$\frac{d^2y}{dx^2} = -A \sum_{i=0}^{\infty} \left(\frac{\pi^2}{L}\right)(-1)^i \sin\left(\frac{(2i+1)x}{L}\right) \sin(\omega_{(2i+1)}t) \tag{8}$$

It should be noted that all the coefficients of the harmonics have the same magnitude of $(\pi/L)^2$. This implies that the curvatures $1/\rho = (d^2y/dx^2)$ induced by the various harmonics are the same. This result, while not intuitively obvious, may be seen graphically with reference to FIG. 1. FIG. 1 shows graphical plots 11, 13, and 15 of the magnitudes of the first, third, and fifth harmonics ($i = 0, 1, 2$) on a relative scale with $A = 25$ units and $L = 30$ units. This implies a radius of curvature $\rho = (1/\pi^2)(L^2/A)$ of approximately 3.65 units which is the common radius of inscribed circles 21, 23, and 25 at the maxima (antinodes) of the respective harmonics. Since $1/\rho = M/\epsilon I = d^2y/dx^2$, this means that at each of the harmonic peaks, the maximum moments are the same, and so are the stresses.

Differentiating Equation 7 with respect to t leads $$\frac{dy}{dt} = A \sum_{i=0}^{\infty} \frac{(-1)^i}{(2i+1)^2} \omega_{(2i+1)} \sin\left(\frac{(2i+1)x}{L}\right) \cos(\omega_{(2i+1)}t) \tag{9}$$

$$= A\omega_1 \sum_{i=0}^{\infty} (-1)^i \sin\left(\frac{(2i+1)x}{L}\right) \cos(\omega_{(2i+1)}t)$$

It should be noted that the coefficients are equal to one, signifying that the maximum particle velocities of each of the modes are all the same. The maximum velocity spectra of the modes are independent of frequency. This is significant in that a velocity transducer is generally equally sensitive to all the modes, and its use becomes important.

Differentiating Equation 7 twice with respect to t leads to:

$$\frac{d^2y}{dt^2} = A \sum_{i=0}^{\infty} \frac{(-1)^i}{(2i+1)^2} (\omega_{(2i+1)})^2 \sin\left(\frac{(2i+1)x}{L}\right) \sin(\omega_{(2i+1)}t) \quad (10)$$

$$= -A\omega_1 \sum_{i=0}^{\infty} (-1)^i (2i+1)^2 \sin\left(\frac{(2i+1)x}{L}\right) \sin(\omega_{(2i+1)}t)$$

The significance of this is that for the higher modes, an acceleration transducer becomes more effective than a velocity transducer.

The above analysis was carried out for the special case of a beam whose both ends were hingedly supported. The boundary conditions then led to the requirement sin kl=0 which is satisfied by values for kL of $\pi$, $2\pi$, $3\pi$, etc. If one or both ends of the beam are clamped or free, the boundary conditions lead to somewhat different requirements on the values of kL. More particularly, it is readily shown that the following constraints on kL arise for the boundary conditions specified:

| | |
|---|---|
| free-free | cos(kL) cosh(kL) = 1 |
| clamped-clamped | cos(kL) cosh(kL) = 1 |
| clamped-free | cos(kL) cosh(kL) = −1 |
| clamped-hinged | tan(kL) = tanh(kL) |
| hinged-free | cos(kL) cosh(kL) = −1 |

While the hinged-hinged case (sin (kL)=0) is the only one which has an exact analytical solution ($kL = n\pi$), the solutions for the other cases share an important attribute, namely nearly equal spacing of the higher modes. More particularly beyond the 4th or 5th mode, the spacing between successive values of kL that satisfy the equation approaches a constant value $\pi$. Thus in some sense, for the higher modes, the particular boundary conditions become unimportant. This implies that the end support conditions are not important when working with the higher modes.

DETAILED DESCRIPTION OF THE INVENTION

FIG. 2 is a schematic illustration of a system 5 according to the present invention as utilized to perform a dynamic stress relieving procedure or an accelerated fatigue testing procedure on a workpiece 10 held in a support structure 12. First and second transducers 15 and 17 are coupled to workpiece 10, and the operation of system 5 is that resonant vibrations are detected by the first transducer (designated the detector) and fed back to the second transducer (designated the driver) to maintain oscillation of the workpiece. More specifically, detector 15 communicates an electrical signal representative of the vibrations to a high pass filter 18, the output of which is amplified by an amplification system including an amplifier 20, and the amplified output is communicated to driver 17 which is coupled to workpiece 10. Amplifier 20 may have associated input and output level monitors 22 and 23 and a gain control 25. A spectrum analyzer 27 may be coupled to the amplifier output to provide information as to which modes are being preferentially excited.

The operation of the system is basically as follows. Resonant vibrations at a large number of the harmonics are excited in workpiece 10 by any convenient means such as applying a small impulse, for example, with a hammer. Of the resonant vibrations sensed by detector 15, at least some of the higher resonant frequencies are amplified by amplifier 20, the output of which is applied to driver 17 to excite workpiece 10. Thus, for some of the frequencies, the feedback is positive so that system 5 functions as an oscillator so that the vibrations of workpiece are self sustaining. It will, however, be appreciated that for any given relative positioning of detector 15 and driver 17, the positive feedback necessary for oscillation will be present for some of the higher modes but not others. Nevertheless, so long as neither detector 15 nor driver 17 is mounted at a location that is a node for all the frequencies of interest, at least some of the higher vibrational modes will be sustained within workpiece 10.

At frequencies on the order of 30 kHz, the vibration waves are generally confined to the surface and propagate relatively freely over the entire surface of the workpiece. Typical wavelengths within this frequency range are on the order of less than a few millimeters, so that substantially the entire surface of the workpiece is subjected to vibrations at at least some of the higher resonant modes, and the points of maximum moment are generally uniformly distributed over the surface. As discussed above, an important feature of the higher modes is that relatively low amplitude vibrations are characterized by a maximum moment that is comparable to the moment produced with a much larger amplitude vibration at the fundamental frequency. Indeed, for the special case of a simply supported beam struck at its center, the maximum moments for all the resonant modes are the same.

The above-described operation of the present invention may be achieved with any convenient sensors or detectors. For example, a sensor whose output signal is proportional to velocity may be used, since, as described above in connection with Equation 9, the maximum particle velocities for all the modes are equal. A suitable sensor that responds to velocity is described in my copending U.S. patent application Ser. No. 963,476, filed Nov. 24, 1978, and entitled "Structural Vibration Sensor," now U.S. Pat. No. 4,314,201 issued Feb. 2, 1982 the disclosure of which is hereby incorporated by reference. Such a sensor utilizes a pickoff coil, so that the product of angular frequency and inductance defines an impedance which tends to determine the upper frequency at which such a sensor provides usable signal. A typical impedance at frequencies in the neighborhood of 30 kHz is about 1000 ohms. In the event that it is desired to operate at higher frequencies, a sensor that is responsive to the acceleration of the particles in the workpiece becomes more effective. For example, a piezoelectric device is suitable. Driver 17 typically utilizes the ame geometry as detector 15, but preferably incorporates low impedance coils (for example 8 ohms) so that it may be driven with conventional audio power equipment. Suitable power amplifiers are manufactured by Kepco, Inc. of Flushing, N.Y., with typical RMS power output of up to several hundred watts.

In view of the above description, a dynamic stress relieving procedure may now be described. Workpiece 10 is first excited with an impulse in order to initiate resonant vibration of workpiece 10. Such initial excitation may actually be unnecessary since the positive feedback in the system may induce spontaneous vibrations. The placement of sensor 15 and driver 17, and the setting on gain control 25 may be varied to achieve a desired level of vibrations within the workpiece. The total amount of vibration is reflected by input and output monitors 22 and 23, while spectrum analyzer 27 provides an indication of which frequencies are being reinforced. It is noted that the type of detector described in the referenced application provides a signal that is proportional to the stress in the workpiece. When the oscillations within workpiece 10 are at a sufficiently high level that the local stress maxima are at least as great as the stresses to be relieved, the level is decreased by suitable adjustment to gain control 25 in order to lower the magnitude of the reversing stresses. In view of the high frequencies involved, a proper relaxation cycle may be effected quickly.

An accelerated fatigue testing procedure will now be described. Broadly, the fatigue testing procedure comprises the steps of inducing resonant oscillations withing workpiece 10 to subject the workpiece to high frequency stress excitations over substantially its entire surface, as described above, and then measuring the length of time until failure occurs. It may be desirable in this application to have the primary excitation at frequencies within a relatively narrow range to facilitate correlations between the time to failure and number of stress cycles.

FIG. 3 is a schematic illustration of the present invention as utilized in a nondestructive testing procedure. Like reference numerals will be used to denote elements corresponding to those in FIG. 2. A structural element 30 to be tested is fitted with a detector 15 and a driver 17 in the same closed loop configuration including high pass filter 18 and amplifier 20. For clarity, monitors 22 and 23, gain control 25, and spectrum analyzer 27 are not shown, it being understood that the system will typically incorporate these elements as above. Broadly, the nondestructive testing procedure utilizes the high frequency vibrational modes of structural element 30 in order to subject the entire surface of the structural element to stresses. These stresses cause high frequency acoustic emissions which are detected by an appropriate detector 35, the output signal of which is passed through a filter 37, designated an ultrahigh pass filter, having a lower cutoff much in excess of the maximum frequency passed by amplifier 20 and filter 18. The signal passing through filter 37 is amplified by an appropriate amplifier 40 and fed to a monitor 42 which may provide an audible, visual, or other indication of the level of very high frequency emissions detected by detector 35. For example, the combined effects of the upper frequency cutoff of detector 15 and amplifier 20, and the lower frequency cutoff of high pass filter 18 might result in an excitation of structural element 30 at frequencies in the range of 10–30 kHz while ultrahigh pass filter 37 would have a lower frequency cutoff close to 1 MHz. Typically, detector 35 would be moved to various places on the surface to detect the acoustic emissions that signify surface microfractures that arise in critical areas of stress concentration and could eventually grow into cracks.

In summary, it can be seen that the present invention provides a surprisingly efficient system for controlling the stresses in solid material to allow a number of procedures to be carried out far more easily, quickly, and cheaply than before possible. While the above provides a full and complete disclosure of the preferred embodiments of this invention, various modifications, alternate constructions and equivalents may be employed without departing from the true spirit and scope of the invention. For example, the use of a separate high pass filter might be obviated if the bandpass characteristics of amplifier 20 are chosen to provide the desired low frequency cutoff. Similarly, different frequency components of vibration may be separated in a network and provided with different phase delays in order to enhance the number of resonant components at which the system provides positive feedback for sustained oscillation. Indeed, standard signal processing techniques may be employed to achieve this result and further adjust the relative amplitudes of the components if required. Therefore, the above description and illustration should not be construed as limiting the scope of the invention which is defined by the appended claims.

I claim:

1. A method of subjecting a structure to stress comprising the steps of:
    determining at least some of the higher resonant frequencies of the structure, said higher resonant frequencies lying above the fourth harmonic; and
    applying stress to the structure at at least one of said higher resonant frequencies to induce stress waves having points of maximum moment at a large number of points on the surface of the structure.

2. The invention of claim 1, and further comprising the step of exciting the structure at a large number of its resonant modes, and wherein said determining step comprises the steps of detecting the resonant vibrations and generating an electrical signal having components at at least some of the higher resonant frequencies.

3. The invention of claim 1, wherein said stress applying step is carried out at a level of stress amplitude exceeding residual stresses within the structure, and further comprising the step of reducing the level of stress in order to relieve the residual stresses within the structure.

4. The invention of claim 1, and further comprising the step of measuring the time during which said stress applying step is carried out in order to determine a characteristic number of stress cycles to which the structure was subjected, such that when said stress applying step is carried out for sufficient time that the structure fails, said time measuring step provides fatigue information.

5. The invention of claim 1, and further comprising the step of detecting acoustic emissions at frequencies above the frequencies characteristic of said stress applying step, such that potential defects may be determined non-destructively without the need for large test loads.

6. A method of subjecting a structure to stress comprising the steps of:
    subjecting the structure to an impulse to excite the various resonant frequencies of the structure;
    detecting the resonant vibrations and generating a signal having components at a large number of the higher resonant frequencies lying above the fourth harmonic;
    amplifying at least one of said high frequency resonant components to produce an excitation signal; and
    inducing stress in the structure with a time dependence corresponding to said excitation signal.

7. A method of subjecting a structure to stress comprising the steps of:
    coupling a detector to the structure to generate an electrical signal representative of resonant vibrations of the structure;

amplifying at least one of the high frequency resonant components lying above the fourth harmonic to produce an excitation signal;

coupling a driver to the structure; and applying the excitation signal to the driver to excite the structure and thus induce stress in the structure;

said detector coupling step, said amplifying step, and said driver coupling step being carried out so that at least one of said high frequency resonant components is positively fed back from the driver to the detector to sustain resonant vibration.

8. The invention of claim 7 wherein said amplifying step is carried out over a range of frequencies lying above about ten kHz.

9. Apparatus for subjecting a structure to stress comprising:

a detector adapted to be coupled to said structure for providing an electrical signal representative of higher resonant frequency vibrations of said structure, said higher resonant frequencies lying above the fourth harmonic;

means for amplifying at least a portion of said signal from said detector to produce an amplified excitation signal; and a driver responsive to said excitation signal and adapted to be coupled to said structure for inducing stress in said structure at frequencies corresponding to the higher resonant frequency components of said excitation signal.

10. The invention of claim 9 wherein said driver and said detector are velocity sensitive transducers.

11. The invention of claim 9, and further comprising selective blocking means for preventing low frequency components being below about ten kHz from being communicated from said detector to said driver.

12. The invention of claim 11 wherein said selective blocking means prevents said low frequency components from being communicated from said detector to said amplifier.

13. The invention of claim 9, and further comprising:

means adapted to be coupled to said structure for detecting acoustic emissions in a frequency range above the high frequency cutoff of said amplifier;

whereby said apparatus may be used for non-destructively testing a structural element in place.

* * * * *